United States Patent
Nürnberg et al.

(10) Patent No.: US 6,565,881 B1
(45) Date of Patent: *May 20, 2003

(54) EFFERVESCENT BATH TABLET, METHOD OF PREPARING IT, AND THE USE THEREOF

(75) Inventors: Eberhard Nürnberg, Uttenreuth (DE); Kerstin Jerzembek, Gross-Umstadt (DE); Rolf D. Beutler, Höchst/Hummetroth (DE); Jürgen Ebinger, Hünstetten (DE); Ruth Weis, Weiterstadt (DE)

(73) Assignee: Marz Pharma GmbH & Co.KgaA, Frankfurt am Main (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 82 days.

(21) Appl. No.: 09/114,796

(22) Filed: Jul. 13, 1998

(30) Foreign Application Priority Data

Dec. 20, 1997 (DE) .......................................... 197 57 059

(51) Int. Cl.[7] .................................................. A61K 9/46
(52) U.S. Cl. ...................... 424/466; 424/401; 424/450; 424/464; 424/44; 424/70.31
(58) Field of Search ................................. 424/466, 401, 424/450, 70.31, 464, 44

(56) References Cited

U.S. PATENT DOCUMENTS

| | | | | |
|---|---|---|---|---|
| 5,110,603 A | * | 5/1992 | Rau | 424/466 |
| 5,478,501 A | * | 12/1995 | Rau | 252/547 |
| 5,766,628 A | * | 6/1998 | Nurnberg et al. | 424/450 |

FOREIGN PATENT DOCUMENTS

| | | |
|---|---|---|
| DE | 21 56 428 | 5/1973 |
| DE | 42 00 002 | 7/1993 |
| EP | 0 312 668 A | 4/1989 |
| EP | 0 498 272 A | 8/1992 |
| EP | 0 557 825 A | 9/1993 |

* cited by examiner

Primary Examiner—Thurman K. Page
Assistant Examiner—Lakshmi Channavajjala
(74) Attorney, Agent, or Firm—Norris McLaughlin & Marcus

(57) ABSTRACT

The present invention relates to a new type of solid balneological preparations for cosmetic, hygienic and therapeutic use, which has both the properties of a solid bath additive and those of liquid products, and is characterized especially by the addition of lipid components, vesicle forming lipids, tensides and, in some cases, mineral salts. Active components, adjuvants such as stabilizers, adsorbing substances, lubricants as well as smoothing and breakdown promoting agents may also be contained therein.

14 Claims, 2 Drawing Sheets

EFFERVESCENT BATH TABLET, METHOD OF PREPARING IT, AND THE USE THEREOF

The present invention relates to a new type of solid bath preparation for cosmetic, hygienic and therapeutic use, which has both the properties of a solid bath salt and those of liquid products, and is especially characterized by the addition of lipid components, vesicle forming lipids, tensides and in some cases mineral salts. They may also contain active components, adjuvants such as stabilizers, adsorbing substances, lubricants, and slippage and breakdown promoting agents.

The invention furthermore relates to the preparation of such products and their use.

Heretofore bath products have been mostly liquid preparations in the form of tenside solutions with the addition of essential oils and other active components, gels, especially for shower bathing, or in the form of dissolved salts. Among the liquid preparations, those tenside products which contain a proportion—possibly a very high proportion—of oils and other fat-like products, are in a class by themselves.

A special advantage of these bath oils is to be found in the fact that they contain vesicle forming lipids as additives and are capable of the spontaneous formation of liposomes (German Patent 42 05 548).

In these liquid preparations, no O/W tensides are normally contained, since they may prevent spontaneous vesicle formation. Only under certain conditions is it possible to make bath preparations with a lipid content and O/W tensides with vesicle forming properties. This is shown in German Offenlegungsschrift 196 02 346.7-41. According to the latter, preparations with a content of more than 30% of lipophilic components and vesicle forming substances can have spontaneous vesicle formation only if a complexation of the O/W tenside is performed with W/O tensides. The molar ratio of W/O to O/W tensides amounts to 1:2 to 1:0.2.

The above-named bath oils are either liquid or semi-liquid, spreadable preparations. However, they contain no electrolytes since the latter might undesirably influence the consistency of the composition. Furthermore, special measures must be taken with regard to the transport and dosing of such products.

Solid bath products, namely bath tablets, which are characterized by the release of $CO_2$ into the bath water due to their effervescent character, are easier to handle from the packaging and transport point of view—especially in the case of glass bottles (injury hazard), and can also contain electrolytes. They are composed of an effervescent combination of carbonate or bicarbonate and an acid, preferably citric or tartaric acid, binders (cellulose derivatives or starch), bursting agents and lubricants (talc, Macrogol (polyethylene glycol), and essential oil additives, perfumes, dyes and tensides.

Carbonic acid not only gives the bath a pleasantly tingling feeling but also has a dilating effect on the blood vessels in the skin, promoting circulation and having a regulating effect on the heat and cold receptors of the skin, i.e., on the organs of touch which convey the feeling of warmth and cold.

Such effervescent bath salts tablets are described in G. A. Nowak, "Die kosmetischen Präparate," 2nd ed., 1975, pp. 672–674 and cover, for example, compositions of sodium carbonate, tartaric acid, talc, sodium hexametaphosphate, potato starch, carboxymethylcellulose, pectin, sodium lauryl sulfate, dyes and perfume oil.

In K. H. Schrader, "Grundlagen und Rezepturen der Kosmetika," 2nd ed. 1989, p. 606, a noneffervescent bath salt of sodium chloride and sodium sulfate is described, and on page 390 of the 1979 edition, effervescent bath tablets of sodium hydrogen carbonate, tartaric and boric acid, wheat starch powder, kaolin, perfume and apple pectin.

As it can be seen from this, bath tablets—especially effervescent bath tablets—contain no tenside-lipid combination with a skin-cleaning and skin-care action.

If it is desired to apply the knowledge obtained from liquid bath preparations regarding the tenside-lipid combination to solid products such as effervescent bath tablets, it will be impossible, since compressed tablets can contain only extremely small amounts of liquid and fats if they are to remain stable.

The addition of liquid or paste lipids and tensides adversely affects the flow and tableting and the galenically relevant properties of the tablets with regard to friability, strength and solubility and makes the production of individually measured solid (medicated) tablets impossible.

The present invention is therefore addressed to the problem of preparing effervescent tablets, known in themselves, such that they will have both the properties of solid effervescent tablets and the properties of fluid baths and oil baths, that is, which contain lipids, vesicle forming additives which will permit spontaneous vesicle formation upon dissolution in water, as well as tensides with O/W and/or W/O emulsifying character, and additional electrolytes, if desired, aside from those which are used as effervescing components.

In this manner, solid bath tablets are to be made with good dispersal qualities in water, with simultaneous emulsification of the lipid component(s) and, if desired, the release of electrolytes on the model of the so-called akratotherms, as well as spontaneous vesicle formation with the formation of a skin-treating, finely porous foam, so that the properties of both solid and fluid products can be combined.

In the solution of this problem, the preparations obtained in the cited patents and patent applications and the literature in connection with the preparation of lipophilic, vesicle-forming bath preparations could not be used. Such products can not be incorporated in the manner that would be necessary for the targeted effervescent bath tablets.

Surprisingly, however, it was found that stable, solid, effervescent bath salt tablets can be made if certain proportions of one or more lipid components of a vesicle forming lipid in combination with W/O and/or O/W tensides are added to the solid effervescent combination of carbonate/bicarbonate and acid. Such products cannot be incorporated in any manner that would be necessary for the desired effervescent bath tablets.

Especially if mineral salts are added, salt media similar to thermal baths can be achieved together with balneological effects of cleansing, healing and body care baths.

Effervescent tablets according to the invention comprise 10–97%, especially 60–92%, of a carbonic/bicarbonic acid mixture, 0–30%, especially 0–10% active components selected from essential oils, perfumes, vitamins, extracts, curative or skin-care substances or mixtures thereof, and 0–10% adjuvants, and they are characterized in that they also contain 0.1–50%, especially 1–25%, of one or more lipid components, 0.1–20%, especially 0.1–5%, of vesicle forming lipids, 0.1–20%, especially 0.1–5%, of one or more O/W and/or W/O tensides, 0–10%, especially 0.1–3%, of a colloid with a molecular mass up to a maximum of 50,000, as well as 0–80% mineral salts.

Preferred tablets include combinations of one or more O/W and W/O tensides, or of one or more O/W tensides in the stated amounts.

Preferred effervescent tablets according to the invention contain 60–92% of the carbonate/acid mixture; 0.1–5% tensides, 1–25% lipid component, 0.1–5% vesicle forming lipids, 0–5% adsorbing substances, 0–10% active components, 0.1–3% albumin hydrolyzate and 0–80% mineral salt.

Especially preferred effervescent tablets comprise

70–92% of the carbonate/bicarbonate mixture, 0.2–5% active components, especially alpine herb extract/combination of camphor, eucalyptus oil, tea tree oil or willow bark extract/methyl nicotinate or green tea extract/rosemary oil, 0–5% adjuvants, such as especially colorants and perfumes, 1–10% of one or more lipids, 0.1–5%, especially 1–4%, of tensides, 0.1–5% vesicle forming lipids, 0.5–2.5% of a colloid, especially a protein hydrolyzate, selected from wheat protein and/or collagen hydrolyzate, plus 4–55% of mineral salts, especially salts of calcium, magnesium, sodium and potassium.

The carbonate/bicarbonate-acid mixture is known and consists usually of 5–80% of carbonate/bicarbonate, preferably 10–50%, such as sodium or potassium (bi)carbonate or ammonium (bi)carbonate, potassium carbonate, as well as 10–80%, preferably 10–50% of an acid, especially an organic acid, such as citric or tartaric acid or fumaric acid or adipic acid or mixtures thereof, or of an acid anhydride such as citric or succinic acid anhydride, or inorganic acid salts such as sodium dihydrogen phosphate, sodium fumarate or mixtures thereof.

The compositions according to the invention can, as mentioned, contain 0–30% of active components or mixtures thereof.

These include essential oils, such as oil of rosemary, eucalyptus oil, tee tree oil, or perfumes such as those commonly used for such purposes, or vitamins such as vitamin E, pantothenic acid, vitamin C, and curative substances with a cutaneous and/or systemic action, such as polidocanol, methyl nicotinate, hydroxyethyl salicylate, urea. Also, skin-care components such as jojoba oil and avocado oil. Depending on the application, the active components can also be combined.

If necessary, adsorbing substances, lubricants, bursting agents, dyes, or other substances common in effervescent tablets, are used in the stated amounts as adjuvants.

Suitable adsorbing substances are especially cyclodextrin, dextrin, starch and/or highly disperse silica or other silicon dioxide products, in the stated amounts.

Suitable dyes are, for example, water-soluble dyes such as cochineal red, patent blue and quinoline yellow.

Suitable lubricants are especially Macrogol, magnesium stearate and talc. Starch products, cellulose derivatives and carboxymethylated, crosslinked povidones can be used as bursting agents.

Used as mineral salts are especially salts of the cations sodium, potassium, magnesium, calcium, iron, ammonium or manganese and the anions hydrogen carbonate, chloride, fluoride, sulfate or nitrate individually or in mixtures. Also, other salts known in thermal bath technology, such as lithium, aluminum and strontium in the cations, and iodide, bromide and thiosulfate for the anions.

Hereby thermal bath conditions can be obtained.

With the above-named mineral salts, especially rock salt and/or sea salt, compositions according to the invention can also be used directly or as granules.

Surprisingly it has been found also that, in spite of the presence of the electrolytes (of the effervescence charge and the mineral salts if desired) neither the spontaneous formation of vesicles nor the skin care and cleaning are negatively affected due to the tenside-lipid mixture.

This spontaneous vesicle formation could not at all be foreseen, because the vesicle forming lipid primarily used is not dissolved in an oil as in the case of the oil baths or in the shower-bath gels, that is, it is not molecularly dispersed, but is added directly in its actual form (liquid, paste or solid) to the tableting material, and furthermore this vesicle-forming lipid, additional lipids and the tensides as well as all other components - each separate from the other—are present in the powder mixture.

That the liposome formation is not affected, either, by the high electrolyte content, was also unforeseeable.

Furthermore, direct tableting is possible in spite of the lipophilic content.

It has furthermore been found that, due to the combination according to the invention, mechanically stable tablets can be made, sometimes also without the common bursting and binding agents. They nevertheless break up sufficiently rapidly in the bath water, they are especially compatible with the skin and gentle, and they have a surprisingly good lipid distribution in spite of the low tenside content. Moreover, in spite of the presence of O/W tensides along with W/O tensides when used, a spontaneous vesicle formation takes place and pleasant, fine-pore suds are formed.

If desired, colloids, especially protein hydrolyzates of plant and/or animal origin, such as for example wheat protein hydrolyzates and collagen hydrolyzates with a molecular mass equal to or less than 50,000, can be incorporated, which have a favorable effect on the formation of liposomes and suds. Other suitable colloids are, for example, polyvinyl pyrrolidone, methyl cellulose and methyl hydroxyethyl cellulose. They are used in amounts of 0–10%, especially 0.1–3%.

With the composition according to the invention, tablets can be made with a high weight, especially 10–300 g, preferably 40–100 g, by mixing the solid starting materials, (partially) granulating them, and combining them and compressing them with liquid components in an appropriate manner, or compressing them directly after mixing and combining all of the components, without granulation.

Furthermore, the composition according to the invention can be used directly in powder crystals or granulated form after all of the components have been mixed and combined.

Especially preferred lipid components, such as can be used in the tablet according to the invention, are for example hydrogenated soya oil, hydrogenated castor oil, hydrogenated peanut oil, partial esters or esters of glycerol, sorbitol, ethylene glycol and propylene glycol, as well as mixed esters including the sorbitan esters, as well as waxes, esters of higher fatty alcohols and/or fatty acids, or mixtures thereof. These include, for example, glycerol monostearate, propylene glycol monostearate, ethylene glycol monostearate, cetyl palmitate or partial esters of sorbitan or mixtures thereof.

It is especially surprising that even larger amounts of up to 50% of lipids can be incorporated into the base without thereby involving galenically relevant disadvantages as regards workability (granulation not essential).

Furthermore, vesicle forming lipids are present according to the invention. Preferred are, for example, lecithin from eggs or soybeans, cholesterol, sitosterol, sphingosine, ceramides, cerebrosides and/or sphingomyelins or mixtures thereof.

In effervescent-type bath tablets containing electrolyte, however, lipids alone are incapable of uniform distribution in the bath water, so that the addition of appropriate tensides or emulsifiers is necessary.

This purpose is accomplished according to the invention by O/W and W/O tensides, especially combinations thereof. Preferred O/W tensides in the form of anionic tensides, include sodium lauryl sulfate, sodium lauryl ether sulfate or carbohydrate tensides or mixtures thereof Appropriate W/O tensides of the low polyoxyethylated fatty alcohol type include macrogol lauryl ethers with 1 to 4 EO units, macrogol(5) oleyl ether, macrogol(7) glycerol cocoate, coconut fatty acid diethanolamide, mono/di/tri-(alkyltetraglycolether)-o-phosphoric acid ester, polyoxyethylene glycol trioleate, or mixtures thereof In W/O-O/W combinations of tensides, refatting tenside complexes form, which provide good compatibility. Such combinations are therefore preferred. The ratio of W/O to O/W tenside depends on the desired emulsification.

Other suitable O/W tensides are polyoxyethylated fatty acids or fatty alcohols, polyoxyethylated esters and partial esters of ethylene glycol, glycerol, propylene glycol or sorbitan. The use of individual or several O/W tensides is likewise preferred. Other suitable W/O tensides are polyoxyethylene sorbitan tristearate and polyoxypropylene (15) stearyl ether.

The added tensides named above have a number of unforeseeable favorable effects on the resultant bath water: for one thing they permit a uniform distribution of the incoherent lipid phase in the bath water, which was unforeseeable on account of the relatively low concentration. On the other hand, they permit, in addition to the cleansing action, the formation of fine-pored suds containing lipids which are soothing to the skin. Furthermore, the formation of liposomes is surprisingly unimpaired by the simultaneous presence of the tensides.

With the effervescent tablets of the invention, baths can be prepared which, due to the effervescence-producing additives, have an enlivening action on the skin and, due to the lipid/vesicle combination, an action restoring oils to the skin. These effects can be further enhanced by the addition of mineral salts and/or active components.

A description will be given below of the manufacture of the effervescent tablet according to the invention, as well as its properties.

1 EXAMPLES OF MANUFACTURE

The products in the following Examples 1–3 were prepared by mixing the solid products and, after subsequent combination with the liquid components, they were pressed directly.

Manufacturing Example 1
(Percentages)

| | |
|---|---|
| Camphor | 0.25 |
| Eucalyptus oil | 0.25 |
| Tea tree oil | 0.50 |
| Alpine herb extract | 1.00 |
| Citric acid | 36.70 |
| Sodium bicarbonate | 37.70 |
| Hydrogenated soybean oil | 7.00 |

-continued

| | |
|---|---|
| Soya lecithin | 1.00 |
| Sodium lauryl sulfate | 1.00 |
| Laureth 2 | 1.00 |
| Wheat protein hydrolyzate | 1.00 |
| Cornstarch | 0.50 |
| Potassium bicarbonate | 1.00 |
| Magnesium carbonate | 1.00 |
| Calcium carbonate | 5.00 |
| Sodium chloride | 2.00 |
| Sodium sulfate | 2.00 |
| Patent blue | 0.10 |
| Perfume oil | 1.00 |

Manufacturing Example 2
(percentages)

| | |
|---|---|
| Vitamin E acetate | 1.00 |
| Vitamin C | 5.00 |
| Calcium pantothenate | 0.50 |
| Willow bark extract | 0.50 |
| Tartaric acid | 42.20 |
| Potassium bicarbonate | 12.20 |
| Sodium carbonate | 30.00 |
| Hydrogenated peanut oil | 1.00 |
| Phospholipids | 2.00 |
| Sodium lauryl ether sulfate | 1.00 |
| Laureth 4 | 1.50 |
| Collagen hydrolyzate | 2.00 |
| Cochineal red | 0.10 |
| Perfume oil | 1.00 |

Manufacturing Example 3
(percentages)

| | |
|---|---|
| Methyl nicotinate | 0.50 |
| Hydroxyethyl salicylate | 0.20 |
| Green tea extract | 1.00 |
| Citric acid | 30.00 |
| Fumaric acid | 14.00 |
| Ammonium carbonate | 9.20 |
| Sodium bicarbonate | 35.00 |
| Hydrogenated castor oil | 5.00 |
| Cyclodextrin | 2.00 |
| Sitosterol | 1.00 |
| Coconut fatty acid diethanolamide | 0.50 |
| Sodium lauryl sulfate | 1.00 |
| Polyvinyl pyrrolidone | 0.50 |
| Quinoline yellow | 0.05 |
| Perfume oil | 0.05 |

II Proof of the distribution of the lipid phase and of liposomes with effervescent tablets according to the invention in Manufacturing Example 1.

BRIEF DESCRIPTION OF THE DRAWINGS

In FIGS. 1 and 2 the situation is represented in electron photomicrographs taken in a bath prepared with the product of Example 1, in which (note the rings) multilaminar (FIG. 1) and bilaminar (FIG. 2) vesicular structures can be seen.

Since lipid droplets (i.e., the distribution of the fatty phase) cannot be shown in the electron photomicrographs on account of their size, polarizing photomicrographs were made of the situation in a bath prepared with the product of Example 1.

Figure 1:
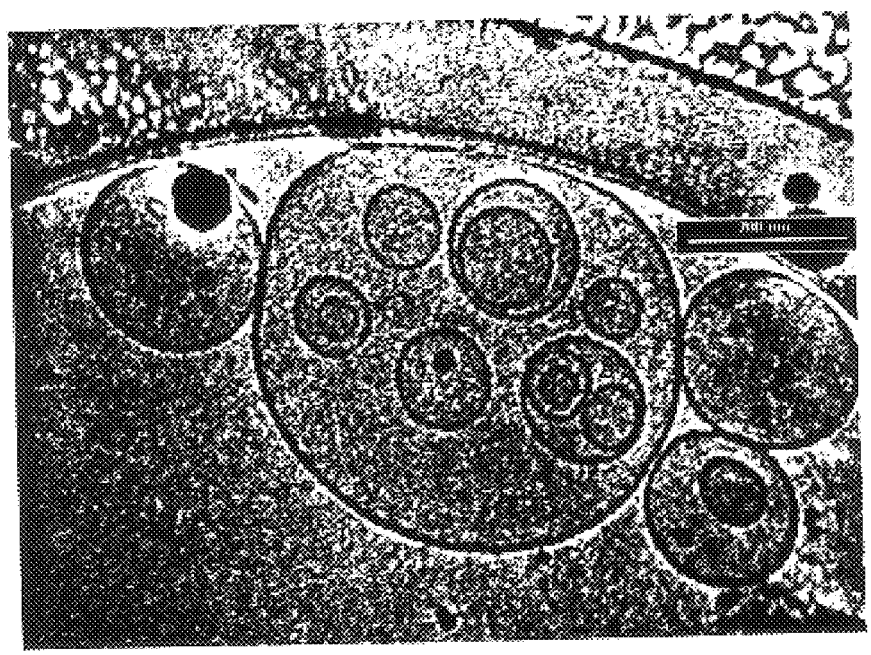
FIGS. 1 and 2 (Electron Photomicrographs)
Figure 2:
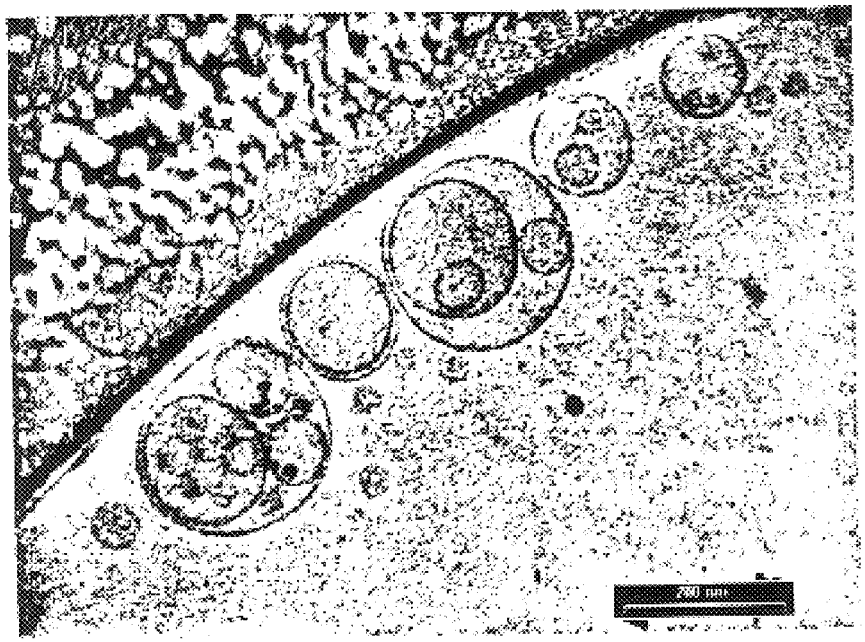
Figure 3:
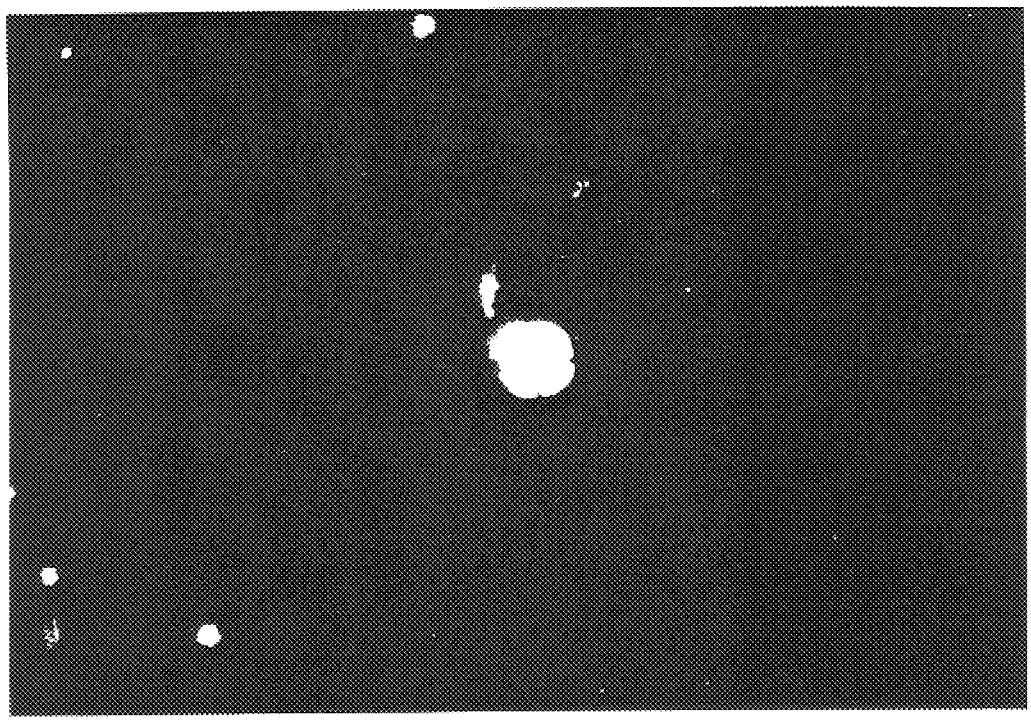
FIGS. 3 and 4 (Polarizing Photomicrographs)
Figure 4:
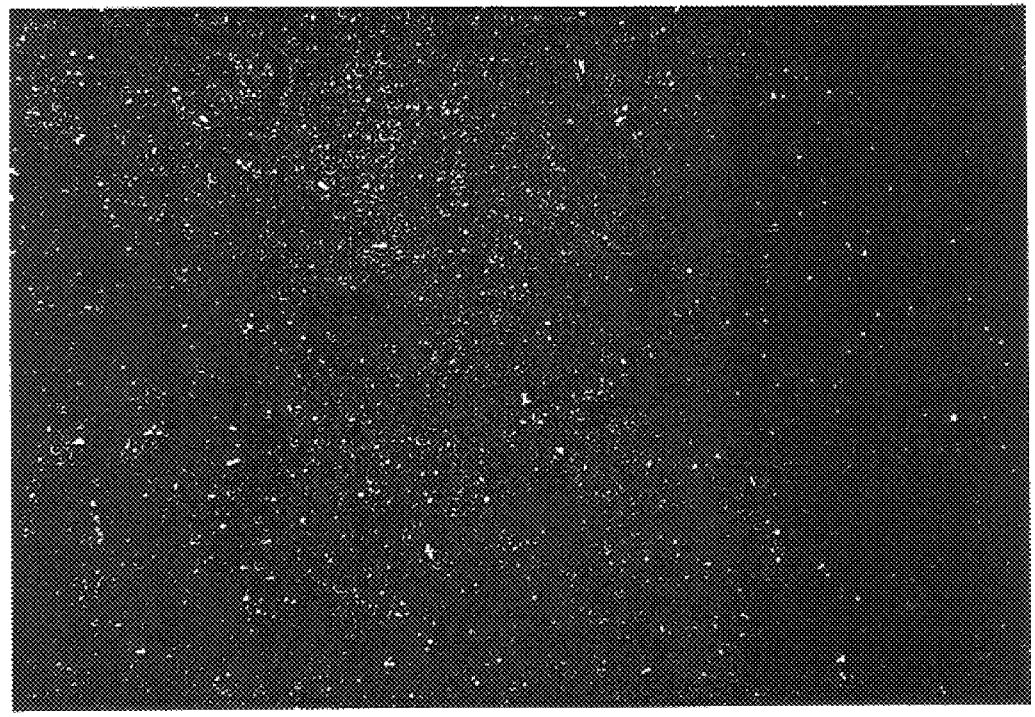

In FIG. 3 the lamellar structures can again be clearly seen (larger white circles), and in FIG. 4 the uniform distribution of the fat droplets.

What is claimed is:

1. Balneological effervescent tablet, comprising:
   a) 10–97% of a carbonate/bicarbonate acid mixture,
   b) 0–30% active components selected from the group consisting of essential oils, extracts, perfumes, vitamins, skin-care and curative substances and mixtures thereof,
   c) 0–10% adjuvants,
   d) 0.1–50% of one or more lipid components,
   e) 0.1–20% vesicle forming lipids,
   f) 0.1–20% of one or more O/W and/or W/O tensides,
   g) 0–10% of one or more colloids with a molecular mass up to maximum 50,000, and
   h) 0–80% mineral salts.

2. Effervescent tablet according to claim 1, further comprising one or more substances with adsorbing properties selected from the group consisting of cyclodextrin, dextrin, starch and highly disperse silica, or one or more adjuvants selected from the group consisting of other silicon dioxide products.

3. Effervescent tablet according to claim 1, further comprising protein hydrolyzates of vegetable and/or animal origin, in an amount of 0–10%.

4. Effervescent tablet according to claim 1, comprising 60–92% of the (bi)carbonate/acid mixture, 0.1–5% tensides, 1–25% lipid components, 0.1–5% vesicle forming lipids, 0–5% adsorbing substances, 0–10% active components, 0.1–3% protein hydrolyzate and 0–80% mineral salts.

5. Effervescent tablet according to claim 1, wherein the mineral salts comprise cations selected from the group consisting of sodium, potassium, magnesium, calcium, iron, ammonium and manganese and anions selected from the group consisting of hydrogen carbonate, carbonate, chloride, fluoride, sulfate and nitrate.

6. Effervescent tablet according to claim 1, which has a total mass of 10–300 g.

7. Effervescent tablet according to claim 1, wherein the lipid components comprise one or more components selected from the group consisting of hydrogenated soya oil, hydrogenated castor oil, hydrogenated peanut oil, partial esters and esters of glycerol, sorbitol, ethylene glycol and propylene glycol as well as mixed esters thereof, as well as waxes, and esters of higher fatty alcohols and/or fatty acids or mixtures thereof.

8. Effervescent tablet according to claim 1, wherein the vesicle-forming lipids comprise components selected from the group consisting of phospholipids, lecithin from eggs or soybeans, cholesterol, sitosterol, sphingosine, ceramides, cerebrosides and/or sphingomyelins or mixtures thereof.

9. Effervescent tablet according to claim 1, which comprises one or more O/W tensides, which are selected from the group consisting of sodium lauryl sulfate, sodium lauryl ether sulfate, polyoxyethylated fatty acids or fatty alcohols, polyoxyethylated esters or partial esters of ethylene glycol, glycerol, propylene glycol or sorbitan, carbohydrate tensides and mixtures thereof, and/or one or more W/O tensides, which are selected from the group consisting of low-polyoxyethylated fatty alcohols.

10. Method of preparing a balneological effervescent tablet according to claim 1, comprising mixing the individual solid components, (partially) granulated and combined in an appropriate manner with liquid components, and pressed or pressing the solid components directly without granulation after the mixing and combining of all components.

11. Effervescent tablet according to claim 1, wherein the carbonate/bicarbonate acid mixture comprises sodium (bi) carbonate, calcium, ammonium or potassium (bi)carbonate or mixtures thereof, and one or more acids selected from the group consisting of citric acid, tartaric acid, fumaric acid, and adipic acid; or one or more acid anhydrides selected from the group consisting of citric acid anhydride and succinic acid anhydride, or one or more acid salts thereof selected from the group consisting of sodium hydrogen phosphate, sodium fumarate, and mixtures thereof.

12. Effervescent tablet according to claim 7, wherein the mixed esters of ethylene glycol and propylene glycol are selected from the group consisting of the sorbitan esters thereof.

13. Effervescent tablet according to claim 9, wherein the low-polyoxyethylated fatty alcohols are selected from the group consisting of macrogol lauryl ethers with 1 to 4 EO units, macrogol(5)-oleyl ethers, macrogol(7)-glycerol cocoate, coconut fatty acid diethanolamide, mono/di/tri-(alkyltetraglycolether)-o-phosphoric acid ester and polyoxyethylene glycol trioleate.

14. A method of achieving a balneological effect comprising adding a balneological effervescent tablet to bath water, wherein the balneological effervescent tablet is an effervescent tablet according to claim 1.

* * * * *

UNITED STATES PATENT AND TRADEMARK OFFICE
CERTIFICATE OF CORRECTION

PATENT NO. : 6,565,881 B1
DATED : May 20, 2003
INVENTOR(S) : Nurnberg et al.

It is certified that error appears in the above-identified patent and that said Letters Patent is hereby corrected as shown below:

<u>Title page,</u>
Item [*] Notice: Subject to any disclaimer, the term of this patent is extended or adjusted under 35 USC 154(b) by (82) days
Delete the phrase "by 82 days" and insert -- by 433 days --

Signed and Sealed this

Twenty-fifth Day of November, 2003

JAMES E. ROGAN
*Director of the United States Patent and Trademark Office*